United States Patent [19]

Micale

[11] Patent Number: 4,665,107

[45] Date of Patent: May 12, 1987

[54] PIGMENT ENCAPSULATED LATEX AQUEOUS COLORANT DISPERSIONS

[75] Inventor: Fortunato J. Micale, Bethlehem, Pa.

[73] Assignee: Koh-I-Noor Rapidograph, Inc., Bloomsbury, N.J.

[21] Appl. No.: 842,609

[22] Filed: Mar. 21, 1986

[51] Int. Cl.$^4$ .................. C09B 67/00; C09D 5/00; C08K 9/00; C08J 3/02
[52] U.S. Cl. .................... 523/105; 523/161; 523/205; 523/211; 523/335; 523/340; 8/527
[58] Field of Search ............... 523/105, 205, 211, 335, 523/340; 8/527

[56] References Cited

U.S. PATENT DOCUMENTS

| | | | |
|---|---|---|---|
| 4,330,460 | 5/1982 | Hoffend et al. | 523/205 |
| 4,339,337 | 7/1982 | Tricot et al. | 524/431 |
| 4,407,985 | 10/1983 | Muller | 523/161 |
| 4,421,660 | 12/1983 | Hajna | 523/202 |
| 4,471,079 | 9/1984 | Enami | 523/161 |
| 4,525,525 | 6/1985 | Hofer et al. | 524/804 |
| 4,530,961 | 7/1985 | Nguyen et al. | 523/161 |
| 4,532,276 | 7/1985 | Knable et al. | 523/161 |
| 4,608,401 | 8/1986 | Martin | 523/205 |

Primary Examiner—Herbert J. Lilling
Attorney, Agent, or Firm—David H. Semmes; Warren E. Olsen

[57] ABSTRACT

A process for modifying colorants which comprise an active ingredient of solid primary particles in the submicron range by an encapsulation with polymer starting materials that are not substantially altered during the process. Writing fluids, textile colorants and cosmetic inks are disclosed wherein the intrinsic physical qualities of a solid active material are modified to create a stable aqueous dispersion with performance and rheology characteristic of the polymer, and not of the active ingredient.

34 Claims, No Drawings

PIGMENT ENCAPSULATED LATEX AQUEOUS COLORANT DISPERSIONS

BACKGROUND OF THE INVENTION

The invention relates to a process for producing submicron-sized particles of polymer encapsulted solid pigments and similar solid active ingredients, wherein a polymer matrix completely surrounds the active ingredient and the resulting particles are configured to have a buoyancy which is either neutral in an aqueous suspension, or chosen for a particular relationship to another ultimate carrier fluid. The present encapsulation technique is disclosed to have three specific applications, in the field of low viscosity aqueous colorants. Historically, the application of a given solid colorants to a substrate, such as paper, textile, or human skin, has required a unique dispersion chemistry.

The first application is production of low viscosity, aqueous writing fluids, wherein the active ingredient comprises a pigment comprised of primary particles in the submicron range, wherein the process is controlled to produce a neutrally buoyant suspension of encapsulated particles within water.

The second application relates to the problem of textile coloration wherein there is need to modify intrinsic characteristics of pigments in order to create a more predictable or uniform action of the colorant upon various textile substrates.

The third application relates to the preparation of cosmetics, wherein a solid active ingredient is modified and a composition is produced which is either film-forming, or non-film-forming, whereby the polymer matrix is adjusted to provide skin interaction characteristics that are independent of those inherent in the encapsulated solid ingredient.

The present invention categorically involves handling of solid particulate matter, in the range 0.001 to approximately 2.0 microns in average diameter. Solids categorized as pigments that have primary particles processed to be submicron in average size are a preferred starting material. In addition, to small primary particle size, the particles need to be dispersed homogeneously within a particular class of solvents and polymers, without any appreciable agglomeration. The present invention also categorically begins with a polymer that substantially is insoluble in water, and does not undergo chemical change to achieve an encapsulated particle. If the polymer substantially retains its physical characteristics during the process, the performance and rheology of a resulting fluid substantially is predictable, without critical change upon substitutions of other solid active ingredients, having similar size and surface characteristics.

The present invention categorically is not an emulsion polymerization, since the primary particles are not dispersed in a monomer or any mixture of monomers, with a polymerization subsequent to the emulsification step. Representative prior art techniques for producing colloidal size hydrophobic polymer particulates that surround discrete particles of inorganic material are discussed by SOLC nee Hajna, (U.S. Pat. No. 4,421,660), which teaches an emulsification polymerization for surrounding discrete primary particles with a polymer matrix, which then are useful for applications similar to the applications taught herein. The present invention categorically avoids need for adjusting conditions of emulsification so as to induce polymerization of a monomer, although the present invention particularly requires a solvent in an intermediate step which must be removed, requiring energy to produce the end product. Unlike suspension polymerization, however, the present invention is capable of encapsulating particles or molecules at very wide concentration ranges, molecule to polymer ratios of from 1/10 to 10/1, by weight, and also capable of employing a wide variety of polymer candidates having widely varying physical properties, under virtually identical process conditions. In other words, since there is no need to establish hospitable conditions for a polymerization of monomer, the present invention requires matching only of physical characteristics of a polymer through the solvent and water components. The choice of surfactants also is greatly simplified since surfactants are known to interfere with polymerization reactions. Emulsion polymerization requires satisfaction of many different variables, which limit the nature and concentration of materials which successfully may be encapsulated. The complexity of emulsion polymerization further requires a new investigation of appropriate conditions to induce a polymerization for a desired concentration and material for each specific application.

Another dispersion polymerization technique employing solid particulate materials is represented by Bayley (U.S. Pat. No. 4,264,700) wherein toner particles are prepared by a suspension polymerization, and both a monomer and a solvent are included for preparation of a discontinuous phase. The monomer is emulsified in order to allow the monomer to migrate through the aqueous medium, and polymerize at active sites on the solid toner particles. It also is known from Nguyen et al. (U.S. Pat. No. 4,530,961) how to create an aqueous dispersion of carbon black for an ink jet writing fluid, by grafting active sites on carbon particles to chains of monomer units. Here again, a simultaneous polymerization and grafting is required.

Removal of the intermediate organic solvent is a critical aspect of the present invention, since a separation or coagulation of the system during an evaporation or distillation step will destroy the desired result. There has existed a need to avoid the unpredictable interactions inherent in dispersion polymerization, so that off-the-shelf polymer candidates can be chosen for their intrinsic physical properties, and substantially contribute those intrinsic properties to encapsulations of various solid particulate materials.

SUMMARY OF THE INVENTION

The present invention teaches how to create a polymer matrix that closely is associated around each submicron primary solid particle, in order to create a resulting low viscosity fluid wherein the fluid's rheology is based substantially upon the inter-relationship of the smooth polymer coating within a water system, with film forming on a given substrate not significantly being affected by the intrinsic properties of the encapsulated pigment.

For a writing fluid application, the present invention may be employed to create a pigment encapsulated latex (PEL), where a homogeneous dispersion of primary pigment particles and polymer, with a surfactant as necessary, creates an initial system which then is dispersed in water to form an emulsion. The water is a continuous phase, and the solvent/polymer/pigment comprises a discontinuous, micron-sized liquid droplet phase. To remove the solvent and define smooth spheres of polymer, the solvent preferably has a vapor pressure higher than water, and solvent distillation is used so as to avoid agglomeration of the discontinuous phase, or any other form of phase separation. The distillation step further enables removal of certain amounts of water to increase solids concentration, without phase separation. Since all pigments are heavier than water, a primary advantage to a PEL dispersion is lowered particle density and increased particle stability, resulting in a final fluid having a more uniform particle concentration than previously has been available.

The present invention requires primary particle sizes, in the submicron range in order to avoid significant viscosity problems in the resultant fluid. Commercial film-forming latexes are available in solubilized or nonsolubilized forms. Solubilized latexes carry a polymer in solution with the consequence that viscosity is a significant function of polymer concentration and its molecular weight. The present invention employs non-solubilized polymer latexes, which are not soluble in a water medium, so that the latex exists in the form of discrete colloidal particles, in the submicron range and also spherical in shape. Accordingly, the viscosity of this form of latex, when dispersed in water, becomes substantially independent of molecular weight and less dependent upon concentration. The densities of polymeric latexes for use in this invention preferably are in the range of 0.9 to 1.1 grams/c.c., since aqueous ink applications require that the combined average density of each encapsulated solid particle should be close to that of the continuous aqueous phase. Further, to the extent that the resultant submicron particles are spherical and smooth, they remain more stable against flocculation, so that a uniform stable dispersion of relatively low viscosity, considering particle concentrations, will result. Manifestly, the systems taught herein will exhibit rheological properties that categorically are unlike those of highly loaded pigment systems, as previously used for writing fluids.

Since the present invention starts with a polymer, and not a monomer, and a polymer which has characteristics of a nonsolubilized latex, the final fluids exhibit physical properties which are typical of a pure latex system, i.e., the encapsulated core material will have virtually no rheological contribution to the behavior of the resulting fluid with respect to a substrate, for example.

Principles of colloidal chemistry teach that particle interaction increases, as particle size decreases. In the present invention, the active solid comprises primary particles having a very small radius of curvature, usually in the particle diameter range of 100 to 300 angstrons with respect to carbon black pigments, for example. Such submicron particles have a tendency to flocculate, and form elongated structures that increase viscosity of the final fluid. Such dispersions also tend to be shear sensitive in a liquid medium of low viscosity, e.g., less than 20 centipoise, whereby flocculation or plugging will occur if the dispersion must flow through a small orifice, as in a technical drafting pen or in a rolling ball pen.

The present invention preferably surrounds individual primary particles with a water insoluble polymer, so that each submicron particle not only is spherical, but tends to have a smooth surface morphogy as a consequence of the surface energy involved. Surface properties of such fluids can be controlled to a greater extent than the surface energy of unencapsulated pigment fluids, since a large number of commercially available polymers are useful for the present invention. The only critical requirement of application of a polymer is that it be substantially insoluble, and preferably less than 5% soluble in water.

While specific examples of the three categories of invention are defined hereinafter, each application begins with dispersing a pigment in a solution of organic solvent and polymer, along with a surfactant chosen primarily for its ability to wet the pigment surface and aid in reducing the interfacial tension between the chosen solvent and water. The pigment should be in the concentration range of 1 percent to 20 percent by weight, of solvent, and the surfactant in the range of 0.1 percent to 20 percent, by weight, relative to pigment. While the surfactant depends substantially upon the surface properties of the pigment, various anionic surfactants generally are preferred. Examples of surfactant types generally useful are: Quaternary ammonium salts, ethoxylated alkyl phenols, ethoxylated alcohols, ethoxylated fatty esters, sulfoccinate derivatives, alkyl aryl sulfonates, sorbitan derivatives. Lecithin and similar naturally occuring mixtures of diglycerides of stearic, palmitic and oleic acids, linked to the choline ester of phosphonic acid are particularly useful surfactant candidates when an FDA approval is involved, as in cosmetic applications. Concentration of polymer, expressed as a polymer to pigment ratio, should be in the range of 1/10 to 10/1. For purposes of this invention, the polymer may either by a film-former or a non-film-former, and be soluble in the chosen organic solvent to create an intermediate solvent/polymer mixture with viscosity of less than approximately 200 centipoise. In turn, the organic solvent must have limited solubility in water, typically less than 20%. The mixing step to disperse pigment in polymer may be accomplished by a variety of techniques suitable for a low viscosity medium, such as ball mill rolling, high speed dispersion, ultrasonic probe vibration, with the primary requirement being that the dispersed solvent/polymer/pigment intermediate mixture is characterized by submicron pigment primary particle sizes homogeneously dispersed.

After this initial mixing step, the intermediate mixture is added to water in a concentration range of 1%–50% by weight, and then emulsified with the preferable techniques being a high speed dispersion by ultrasonic probe. For acceptable emulsification with ultrasonics, the interfacial tension between organic solvent and water should be less than 10 dynes/cm., and preferably less than 5 dynes/cm. Depending upon the total system, the addition and dispersing step may require addition of a further surfactant, in the water phase, in order to reduce the interfacial tension to this level. As a matter of control, the average discontinuous liquid phase droplet size in the resulting emulsified dispersion should be found less than 4 micrometers, and stable for at least two hours after its preparation.

The solvent removal step is preferably done as a distillation, through use of a roto-vapor, by direct evaporation to air, or any other equivalent means of solvent distillation or extraction. If the mixing and dispersing step has resulted in a sufficiently homogeneous mixture, and the addition and dispersing step has created an emulsion with discontinuous phase being submicron in size with respect to the aqueous continuous phase, the danger of phase separation or flocculation upon distillation can substantially be controlled by the pigment/polymer concentration. Each discontinuous phase droplet preferably has one or more primary particles and sufficient polymer exists to coat all suspended particles completely. After the solvent removal step, the aqueous suspension of submicron encapsulated particles further may be concentrated to a desired writing fluid level by evaporation of water, which may either be slow or fast in view of the inherent stability of the aqueous suspension fluid produced by the basic process.

I. Writing Fluid

The following example illustrates a preferred writing fluid embodiment.

EXAMPLE I

PEL (Pigment Encapsulated Latex) Writing Fluid

An organic solvent of 15.0 g of methylene chloride, and 0.10 g 2-amino-2-methyl-1-propanol, is mixed with 3.63 g of an alkylated vinylpyrrolidone copolymer, Ganex V-516 (GAF). Into this mixture is dispersed 0.75 g of the water insoluble pigment, Hostaperm Blue BN-01 (American Hoechst—pigment blue 15:4). The pigment is dispersed in the solvent system using an ultrasonic probe until microscopic examination of the fluid reveals no appreciable pigment agglomerates in the fluid.

A separate water mixture of 25.0 g deionized water, 0.10 g of an anionic surfactant comprising dicotyl sodium sulfosuccinate, Aerosol OT-75 (American Cyanimid), and 0.10 g of a 33% solution of styrene maleic anhydride in aqueous ammonia, SMA 1440H (Arco Chemical) is made. The organic solvent mixture is then emulsified into the water mixture using an ultrasonic probe until the solvent phase emulsion drops are uniform and below 4 micron diameter. The resulting fluid comprises (by weight) approximately 33% solvent, 8% polymer, 2% pigment and 56% water.

The resulting fluid is then mixed on a magnetic stirrer until the methylene chloride is removed from the fluid by evaporation. The final writing fluid is comprised of a dispersion of submicron polymer particles containing one or more pigment particles in a water system, which comprises (by weight) approximately 8% polymer, 2% pigment and 89% water.

II. Textile Coloration

This aspect of invention relates to a new form of colorant particularly both useful for processing raw textiles, and finishing textiles.

When a textile colorant is the desired end product, the important criteria are to adapt different pigment colorants to have similar qualities of washfastness, rubfastness and absorbancy, regardless of the separate wetting characteristics of fibers in a blended textile. If the colorant carrier fluid is water, it also may be desired to have pigment particles that are neutrally buoyant, and a surrounding polymer matrix that has a relatively low glass transition temperature (Tg). In a first thermoplastic textile colorant embodiment, an iron or equivalent heat source is used to fix the colorant by softening the polymer matrix. In a second thermosetting embodiment, an epoxy form of resin is used and a curing agent is introduced either through a one-bath or two-bath textile treatment sequence.

In dye padding, a colorless textile material has a coloring applied prior to final printing of ornamental indica upon the textile product. At the present time, dye padding operations are done at high temperatures (200 degrees C.), and a change in either alkaline or acidic conditions are relied upon to induce reaction between the color material and the fabric. The need to adjust pH to induce the required chemical reaction and the consequent effluent problems for process liquids presents a hazard and a cost which the industry would like to avoid. One well known process for dye padding is the Thermasol process, wherein colorants insoluble in a carrier fluid are dispersed upon the surface and a high temperature treatment is applied to penetrate the color into the fabric.

In subsequent textile processing operations, such as a waterbased polymer is used to achieve film forming, and reformulations are required to match each film-forming agent with a particular colorant and the material.

Migration of colorant is a problem in textile processing because of the different affinities of different colorants for different fabrics, and especially where more than one fiber material is blended, such as polyester/cotton blends. In view of the high temperatures required, and the drastic chemistry required in order to induce interaction between a dye and a fabric, (and the consequent waste effluents which are produced), there has existed a need for a new textile colorant procedure. Preferably, a new procedure is at a lower temperature, and without need for compatability engineering to match the chemistries of different colors, and the widely different colorant absorbtion of composite fiber fabrics such as polyester/cotton blends.

Two basic categories of textile colorations are disclosed. The first comprises thermoplastic colorants, wherein the submicron latex particles surround the solid colorant material, usually a pigment. Fixation to the fabric requires a temperature in excess of the glass transition temperature (Tg) of the polymer matrix which surrounds the colorant particles.

A second category comprises thermosetting textile colorants, and require polymer resins of the epoxy type and a curing agent, which converts the epoxy resin into a thermoset color layer when the polymer is subjected to a temperature above its glass transition temperature. A single bath system, with a water soluble curing agent mixed together with an epoxy resin mixture is most compatible with current textile dyeing operations, although a two-bath system and a water dispersible curing agent also are contemplated.

As in the case of a PEL writing fluid, the film-forming characteristics of the resulting textile colorant substantially is defined by the morphology of the polymer matrix, and not by any characteristic of the encapsulated pigment. Therefore, different core materials will have significantly less impact upon the reaction of the colorant to any given fabric, and the colorant interaction to different fibers within a given blend fabric. It is currently a major problem to predict the exact coloration of a colorant for a blended material, such as 80% cotton, 20% polyester, since the strands of each fiber tend to react significantly different to different colorants.

If a textile colorant system allowed different colorants to be encapsulated within identical or very similar polymer matrices, then for various colors a significantly equivalent color fastness would be achieved, based upon the fabric/polymer interaction. The polymer also could establish a similar interaction between a given color and different fiber components of blend fabrics, since specific wetting agents can minimize preferential polymer wetting on different fiber components of a blend material, and also minimize the differences in polymer capillary travel along different fibers. Hence, for a given polymeric latex coating, many different color pigments, and combinations thereof, are possible if the resultant, submicron sized particles comprise polymeric coatings having the same surface morphology, and are of substantially the same size, regardless of variations in size of characteristic of the core materials.

Therefore, when primary colorants are mixed together to define a new color, an equivalence of coating and particle size would enhance randomness of the resultant dispersion, thereby avoiding concentrations of color hue at different locations of the batch. The present invention saves reformulating a colorant bath for any change in the color, if all pigment component particles coated in a substantially equivalent way to those of standard mixture, having known wetting characteristics to a given fabric.

A. Thermoplastic PEL Colorants

The polymer may be chosen substantially upon its ability to dissolve in a given solvent, and surround submicron primary particles of a colorant. Various forms of polymers commercially available, are candidates, provided the polymer substantially is insoluble in water, and preferably less than 5% soluble in water. Preferred candidates are styrene/maleic anhydride copolymers which can be completely dissolved in organic solvents such as methylene chloride. Also useful are those thermoplastic resins which have a low glass transition temperature (Tg), and preferably around 100 degrees C. In this way, relatively low temperatures are required for flowing the polymer matrix, and forming a film of colorant upon the textile substrate.

B. Thermosetting PEL Colorants

The polymer is a resin of the epoxy-type that reacts to a curing agent to become thermoset after application to a fabric, and exposure to a heat level sufficient to bring the polymer matrix above its glass transition temperature. The epoxy resin/curing agent chosen must be compatible with the aqueous suspension of the final fluid, and the curing agent must be capable of migrating through the aqueous suspension, and curing the exposed surfaces of each polymer particle. Preferred epoxy resins are those of the bisphenol-A-glycidyl ether type, with catalyst curing agents of the modified aliphatic amine type.

Use of a thermosetting PEL textile colorant may be through a one-bath mixing, wherein the color concentrate in aqueous solution includes a water soluble curing agent and a cationic surfactant. The surfactant primarily functions to reduce interfacial tension between the pigment and the surrounding polymer, and also to reduce the interfacial tension between the solvent and water. The first step dispersion of pigment and polymer also can be accomplished with an anionic surfactant, although such dispersions may interact with curing agents having a cationic nature, and flocculation of the suspended particles in a one-bath system may result.

In order to evaluate coloration characteristics; washfastness of a two-bath system; the effect of anionic versus cationic dispersions of colorant; the effect of water soluble versus water-dispersable curing agents; and the effect of a drying between each of the two baths, a series of eight samples was produced. Color value measurements were made by following a standard from AATCC Test Method 61-1980, using a Macbeth RD514 reflection densitometer. Measurements were made initially after coloring, and times after washings according to the standard of Evaluation Test No. IIA (immediately three days and one week after the coloring). Color value readings (the average of three readings) as made on the cyan channel of the densitometer are given in TABLE I.

TABLE I

| Blend | Polyester/ Cotton | ANIONIC PEL | | | | CATIONIC PEL | | | |
|---|---|---|---|---|---|---|---|---|---|
| | | Undried | | Dried | | Undried | | Dried | |
| | | 0/100 | 80/20 | 100 | 80/20 | 0/100 | 80/20 | 0/100 | 80/20 |
| EPI-CURE W50-8535 water-soluble | initial | 55 | 48 | 52 | 50 | 52 | 48 | 52 | 50 |
| | IIA immed. | 52 | 44 | 41 | 46 | 33 | 41 | 51 | 45 |
| | IIA 3 day | 53 | 48 | 45 | 48 | 54 | 46 | 54 | 47 |
| | IIA 7 day | 56 | 49 | 53 | 48 | 53 | 48 | 53 | 49 |
| EPI-CURE 874 water-dispersible | initial | 56 | 44 | 58 | 48 | 50 | 49 | 53 | 49 |
| | IIA immed. | 57 | 44 | 45 | 47 | 38 | 41 | 37 | 45 |
| | IIA 3 day | 58 | 42 | 55 | 47 | 41 | 47 | 42 | 47 |
| | IIA 7 day | 58 | 45 | 54 | 47 | 44 | 48 | 50 | 48 |

This parametric evaluation indicates better overall wash fastness for samples cured with a water soluble curing agent than with a water dispersible curing agent. Initially, colorants which are dispersed with cationic surfactants appear to show better color matching between 100% cotton and 80/20, polyester/cotton blends than textile colorants that initially were anionically dispersed. Immediate washfastness is shown to be better for an anionic colorant that was not dried between baths, while a cationic colorant does better immediate washfastness when dried between baths. This is probably the result of curing agent being absorbed by the fabric in a regulation by wetting characteristics of the cationic curing agent and surfactants present in the colorant dispersions. TABLE I shows that this effect is most pronounced with water-soluble curing agents.

From this test, cationic dispersions of colorant in combination with a water-soluble curing agent appear to provide the best color matching and washfastness for various applications.

To evaluate the effect of epoxy resin-type and its glass transition temperature (Tg), with respect to fastness and overall performance of the colorant, 3 cationic colorants were made, wherein a basic solid epoxy resin was mixed with an equal part of 4 different liquid resins, of different viscosities. A two-bath system was used for the resulting resin mixtures, and washfastness tests of fabric dyed with the 3 mixed resin dispersions showed substantial equivalence and performance. Rubfastness was slightly better for the resin base having the highest viscosity of liquid resin component, which in turn produced the hardest cured film on the fabric. With respect to the life of single-bath systems, containing a water-soluble curing agent, it has been found that the useful life of a one-bath system is significantly longer than expected, after initial mixing of the curing agent. It is believed that total curing of the resin does not occur until submicron particles are applied to the fabric, and the water is removed during the drying step incident to applying the colorant. Even several hours after an initial mixing, washfastness immediately after coloring is equivalent to washfastness in a two-bath, or a just mixed, single-bath.

It has been found that small amounts of color migration or streaking may be minimized by addition of nonionic wetting agents to the bath, which minimizes preferential wetting of the colorant on different fibers within a composite material, and also minimizes the capillary effects of such fiber structures.

The thermoplastic resins discussed hereinbefore also can be applied to a fabric by conventional screen printing, or formulated as a liquid colorant for a pen equipped with a fiber brush. A design could be drawn on a fabric, and then permanently affixed by application of heat through an iron.

The following examples illustrate preferred embodiments of a thermoplastic PEL textile colorant and a thermosetting PEL textile colorant.

EXAMPLE 2

A. Textile PEL (thermoplastic)

An organic solvent of 15.0 g methylene chloride and 0.05 g 2-amino-2-methyl-1-propanol is made. Into this is dissolved 2.00 g of a solvent soluble styrene/maleic anhydride copolymer resin, SMA 3000 A (Arco Chemical). When the SMA resin is completely dissolved, 0.50 g of a water insoluble pigment Hostaperm Blue BN01 (American Hoechst—pigment blue 15:4) is dispersed into the solvent system using an ultrasonic probe until microscopic examination of the fluid reveals no appreciable pigment agglomerates in the solvent/resin/pigment system.

A separate mixture of 25.0 g deionized water, 0.10 g of an anionic surfactant, OT-75 (American Cyanimid) and 0.10 g of a 33% solution of styrene maleic anhydride in aqueous ammonia, SMA 1440H (Arco Chemical) is made. The organic solvent mixture is then emulsified into the water mixture using an ultrasonic probe until the solvent phase emulsion drops are uniform and below 4 microns diameter. The resulting fluid comprises (by weight) approximately 35% solvent, 1% pigment, 4.7% resin and 58% water.

The resulting fluid is then mixed on a magnetic stirrer until the methylene chloride is removed from the fluid by evaporation. The final fluid is comprised of a dispersion of submicron polymer particles containing one or more primary pigment particles, in a water system, which comprises (by weight) approximately 1.6% pigment, 7.3% resin and 91% water.

The resulting colored latex may then be used for the coloration of textile materials using dyeing techniques or formulated into a textile printing ink. The colored latex particles will attach to the fabric fibers after application by exposing the colored fabric or fiber to a temperature above the glass transition point of the polymer matrix surrounding each resin particle.

EXAMPLE 3

B. Textile PEL (thermosetting)

An organic solvent mixture of 15.0 g methylene chloride, 0.20 g of an nonionic surfactant, Surfynol TG (Air Products), 0.20 g of a cationic surfactant, Katapone VV 328 (GAF), and 0.05 g. of a nonionic fluorocarbon surfactant, Zonyl FSN (Dupont) is made. Into this mixture are dissolved epoxy resins comprising bisphenol-A glycidyl ether, 1.25 g of Epi-Rez 510 and 0.75 g Epi-Rez 520 (Celanese). After the resins are completely dissolved, 0.50 g of the water insoluble pigment Hostaperm Blue BN-01 (American Hoechst-pigment blue 15:4) is dispersed into the solvent/resin mixture using an ultrasonic probe until microscopic examination reveals no appreciable pigment agglomerates in the fluid.

This fluid is then emulsified in 25.0 g of deionized water until the solvent phase emulsion drops are uniform and below 4.0 micron diameter. The resulting fluid comprises (by weight) approximately 35% solvent, 1% pigment, 4% resins, and 58% water.

The resulting fluid is then mixed on a magnetic stirrer until the methylene chloride is removed from the fluid by evaporation. The final fluid is comprised of a dispersion of submicron polymer particles containing one or more pigment particles in a water system, which comprises (by weight) approximately 2% pigment, 8% epoxy resins and 89% water.

The resulting colored latex may then be used in applications similar to those stated in EXAMPLE 2, upon the addition of 83 phr (parts/hundred/resin) of a water soluble, curing agent comprising a modified aliphatic amine, Epi-Cure W50-8535 (Celanese). The system will become thermoset after application to the fabric and exposure to heat.

III. COSMETICS

Pigment behavior is a significant cause of cosmetic product variations. Evaluating categories of polymer materials as useful for cosmetic compositions includes determining whether a film forming, or non-film forming fluid best suits the application. Food Drug and Cosmetics Act interpretations have precluded cosmetic use of certain pigments, such as carbon black, and the formulations of a given cosmetic color necessarily requires all active ingredients to be predictable, in various human interaction possibilities.

The preference, for a dense black eyeliner fluid, for example, has led to substantial reliance upon fine particles of black iron oxide as a pigment. Similarly, the preference for red in cosmetic formulations has led to a substantial reliance upon fine particles of red iron oxide. Unlike a writing fluid, cosmetic colorants for use in liquid eyeliners, for example, may employ a non-film forming polymer as well as a film-forming polymer. Other cosmetics may be fluids with relatively high viscosities, or be thixotropic for easier application to the skin, as by brush or as a stick. The cosmetic applications taught herein enable formulation of cosmetics with substantial reliance upon the morphology of an individual polymer matrixes, that preferably totally encapsulate all individual, submicron sized, primary pigment particles. More homogeneous cosmetics are possible if all pigment is encapsulated to present an equivalent size for an equivalent specific density, in the final carrier medium.

The cosmetic process for a liquid eyeliner initially proceeds substantially according to the mixing and dispersing steps recited for a liquid ink writing fluid. The nature of the preferred solvents and the pigments tend to require one or more nonionic surfactants as indicated in the examples hereafter, and both water soluble and non-water soluble surfactants.

In certain cosmetic applications it is desired to separate solid colorant particles, and not to establish a substantially neutrally buoyant pigment/polymer matrix, in water. Very heavy pigments may have a tendency to be kicked-out of the discontinuous solvent phase during the dispersing step and may be recovered by settling, since the lower density of encapsulated pigment resists a settling tendency. The presence of some flocculates in certain applications appears to relate to the hydrophillic nature of pigments such as black iron oxide, and the difficulty of completely dispersing pigments in the discontinuous liquid droplet phase. Insofar as the resulting encapsulated particles are to be dried to a powder form, and remixed in a new cosmetic base material, such complications are not problematic.

Hence, in the category of cosmetic applications, the encapsulation dynamics may be altered significantly, in order to create final products with different rheological characteristics. Nonetheless, the encapsulation aspect significantly removes pigment behavior as an unwanted variable.

Preferred cosmetic applications are illustrated by the following examples, which relate to pigment-encapsulated latex forms of liquid eyeliner inks.

EXAMPLE 4

A. PEL Liquid Eyeliners 1. (Non-Film Forming) A mixture of 13.0 g of the organic solvent methylene chloride and 0.10 g of the nonionic surfactant, Span 60 (ICI Americas) is made. Into this mixture is dissolved 1.00 g of the polymer, polystyrene (MW 230,000). After the polymer is completely dissolved, 1.00 g of the water insoluble iron oxide pigment, Williams red iron oxide PR-34 (pigment red 101) is added and dispersed using an ultrasonic probe until microscopic examination reveals no appreciable pigment agglomerates in the fluid.

Separately, a mixture of 56.0 g of deionized water and 0.25 g of the nonionic surfactant, Lipal 4LA (PVO International) is made. The organic solvent/polymer/-pigment mixture is emulsified into the water mixture using an ultrasonic probe until microscopic examination reveals the solvent phase emulsion drops to be uniform and of a size to contain an average of one pigment particle each. The resulting fluid comprises (by weight) approximately 23% solvent, 1.8% polymer, 1.8% pigment and 72% water.

The resulting fluid is stirred on a magnetic stirrer until the methylene chloride is removed from the fluid by evaporation.

The final fluid is comprised of a dispersion of submicron polymer particles containing one or more pigment particles as well as a fraction of non-pigmented polymer particles, in a water system, which comprises (by weight) approximately 2.6% polymer, 2.6% pigment, and 94% water. The encapsulation of the iron oxide pigment results in a stabilization of the pigment dispersion and slows the settling rate of the colorant, due to the lower density of the encapsulated pigment particles.

The pigment concentration of the final fluid may be concentrated by allowing the colorant to settle and decanting the non-colored supernatant.

EXAMPLE 5

2. (Film-Forming) A mixture of 8.5 g of the organic solvent ethyl acetate and 0.2 g of the nonionic surfactant, Span 20 (ICI Americas) is made. Then, 2.50 g of an alkylated vinylpyrrolidone polymer, Ganex V-516, (GAF), from which the isopropyl alcohol has been removed, is dissolved in the solvent mixture. After the polymer is dissolved, 0.60 g of a water insoluble pigment, PK-4 black iron oxide (Fine Pigments Inc.) is added and dispersed with an ultrasonic probe. Acceptable dispersion is determined when pigment agglomerates are seen under microscopic examination to easily disperse when the fluid is sheared between two microscope slides.

Separately, a mixture of 60.0 g of deionized water and 0.15 g of a nonionic surfactant, lecithin is made. The solent/polymer/pigment mixture is emulsified into the water mixture using an ultrasonic probe until microscopic examination reveals the solvent phase emulsion drops are under 4 microns in diameter. Non-pigmented polymer particles and unencapsulated pigment are noted to be present in noticeable quantities. The resulting fluid comprises (by weight) approximately 12% solvent, 3.5% polymer, 0.8% pigment and 83% water.

The resulting fluid is stirred with a mechanical, non-magnetic stirrer until the ethyl acetate is removed from the fluid by evaporation.

The final fluid is comprised of encapsulated pigment, unencapsulated pigment, and non-pigmented polymer particles, in a water system, which comprises (by weight) approximately 4.4% polymer, 1% pigment and 94% water. The unencapsulated pigment will settle in the fluid, allowing concentration of the encapsulated colorant concentration. The colorant is flocculated though it can be dispersed relatively easily by shaking with agitation.

While three categories of invention have been shown and described, the invention is to be defined and limited solely by the scope of the appended claims.

I claim:

1. A process for producing a colorant comprising a stable aqueous suspension of submicron sized particles of polymer encapsulated active ingredient, wherein a polymer matrix surrounds a core of solid active ingredient, said process comprising the steps of:

A. Mixing together an organic solvent, a polymer soluble in said solvent but substantially insoluble in water and an active ingredient which substantially is insoluble in water to form a homogeneous mixture, wherein said solvent is characterized by a vapor pressure higher than water and said mixing is continued until said active ingredient has dispersed in said solvent without appreciable agglomeration; and B. Adding said solvent/polymer/active ingredient mixture to water, in a concentration range of 1.0% to 50.0%, by weight, and dispersing until an emulsion results wherein solvent/polymer/active ingredient comprises a discontinuous phase, having a size less than 4 microns with water as the continuous phase, werein said dispersing step is done under conditions where interfacial tension between the organic solvent and the water is less than approximately 10 dynes/cm.; and C. Removing substantially all of said solvent to define an aqueous suspension of said particles.

2. The process according to claim 1, wherein, in said mixing step, the polymer is soluble to less than 5 percent, in water, and the solvent is soluble to less than 20% in water.

3. The process according to claim 2, wherein, in said mixing step, the active ingredient comprises solid primary elements having an element average diameter range of between 0.01 to 1.0 microns, and at least one primary element is encapsulated as a core within each polymer matrix wherein, further, the concentration ratio, by weight, of polymer to encapsulated material for each submicron sized particle is between 0.1 and 10.0, and each particle density is controlled by the pigment to polymer ratio.

4. The process according to claim 2, wherein said dispersing step further comprises the addition of a surfactant, in the range between 0.1 percent and 20 percent, by weight, of active ingredient material, and the concentration ratio, by weight, of polymer to encapsulated active material for each particle is between 0.1 and 10.0.

5. The process according to claim 2, wherein, in said mixing step, the concentration, by weight, of active material to solvent is between 1.0 percent and 20 percent, said polymer has a viscosity of less than 200 centipoise when dissolved in said solvent and said dispersing step is done ultrasonically, until substantially each droplet of discontinuous phase comprises a submicron sized polymer matrix encapsulating active material as a solid core.

6. The process of claim 2 wherein said polymer is a system of epoxy resin and a curing agent, said dispersing step conditions are created by a surfactant that is cationic, and said curing agent migrates through the aqueous suspension to cure the surface of each dispersed polymer particle.

7. The process of claim 6 wherein said solvent removal step further comprises applying heat to cure said polymer and remove some or all of the water of said aqueous suspension.

8. The process according to claim 2 wherein, in said mixing step, said polymer is selected from the group consisting of polyvinyl butyral, vinyl acetal polymers, butyrals, styrene/maleic anhydride copolymers, and alkylated vinylpyrrolidone copolymers.

9. The process according to claim 2 wherein, in said mixing step, the polymer has a viscosity of less than 200 centipoise when dissolved in a solvent which is selected from the group consisting of ethyl acetate, methyl isobutyl ketone, methylene chloride, and tetrachlorethylene.

10. The process according to claim 4, wherein said surfactant is selected from the group consisting of quaternary ammonium salts, ethoxylated alkyl phenols, ethoxylated alcohols, ethoxylated fatty esters, sulfosuccinate derivatives, alkyl aryl sulfonates, sorbitan derivatives and lecithin.

11. A process for producing a writing fluid comprising a low viscosity aqueous suspension of submicron sized particles of polymer encapsulated pigment, wherein a polymer matrix surrounds a solid core of pigment, said process comprising the steps of:

A. Mixing together an organic solvent, a film-forming polymer soluble in said solvent but substantially insoluble in water and a pigment comprising submicron sized primary particles, which substantially are insoluble in water, to form a homogeneous mixture, wherein said solvent is characterized by a vapor pressure higher than water and said mixing is continued until said pigment has been dispersed homogeneously as primary particles in said solvent without appreciable agglomeration; and B. Adding said solvent/polymer/pigment mixture to water, in a concentration range of 1.0% to 50.0%, by weight, and dispersing until an emulsion results wherein solvent/polymer/pigment droplets with an average diameter less than 2 microns comprise a discontinuous phase in water as the continuous phase, wherein said dispersing step is done under conditions where interfacial tension between the organic solvent and the water is less than approximately 10 dynes/cm., and substantially each droplet of discontinuous phase has one or more primary pigment particles therein; and C. Removing substantially all of said solvent to define an aqueous suspension of submicron-sized particles of pigment with smooth outer polymer surfaces.

12. The process according to claim 11, wherein, in said mixing step, the polymer is soluble to less than 5 percent, in water, the solvent is soluble to less than 20% in water, and the amounts of polymer/pigment in said mixing step have a combined average density of approximately 1.0 gram/c.c.; wherein further the concentrations of polymer and pigment are chosen so that substantially all of said pigment remains in the discontinuous liquid phase, during said dispersing step.

13. The process according to claim 12, wherein, in said mixing step, the pigment comprises solid primary elements having an element average diameter range of between 0.01 and 1.0 microns, substantially one primary element is encapsulated as a core within each polymer matrix wherein, further, the concentration ratio, by weight, of polymer to encapsulated pigment for each resulting particle is between 0.1 and 10.0, and each particle further has a density in the range of 0.9 to 1.1 grams/c.c.

14. The process according to claim 12, wherein said dispersing step further comprises the addition of a surfactant, in the range between 0.1 percent and 20 percent, by weight, of active ingredient material, and the concentration ratio, by weight, of polymer to encapsulated pigment for each resulting particle is between 0.1 and 10.0.

15. The process according to claim 12, wherein, in said mixing step, the concentration, by weight, of pigment to solvent is between 1.0 percent and 20 percent, said polymer has a viscosity of less than 200 centipoise when dissolved in said solvent and said dispersing step is done ultrasonically, until substantially each discontinuous phase droplet average diameter is below 2 microns in size and comprises a solvent/polymer matrix encapsulating pigment as a solid core.

16. The process according to claim 14 wherein, in said mixing step, said film-forming polymer is of a concentration and molecular weight to have a viscosity of less than 200 centipoise when dissolved in a solvent selected from the group consisting of ethyl acetate, methyl isobutyl ketone and methylene chloride.

17. The process according to claim 16, wherein, said surfactant is selected from the group consisting of quaternary ammonium salts, ethoxylated alkyl phenols, ethoxylated alcohols, ethoxylated fatty esters, sulfosuccinate derivatives, alkyl aryl sulfonates, and sorbitan derivatives.

18. A writing fluid made according to the process of claim 17.

19. A process for creating a textile colorant which comprises creating a polymer matrix that surrounds a core of solid colorant, said process comprising the steps of:
   A. Mixing together an organic solvent, a polymer soluble in said solvent but substantially insoluble in water and colorant primary particles, wherein said solvent is characterized by a vapor pressure higher than water and said mixing is continued until said colorant has been dispersed as primary particles in said solvent without appreciable agglomeration; and
   B. Adding said solvent/polymer/colorant mixture to water, in a concentration range of 1.0% to 50.0% by weight, and dispersing until an emulsion results wherein solvent/polymer/colorant comprises a discontinuous droplet phase in water as the continuous phase, wherein said dispersing step is done under conditions where interfacial tension between the organic solvent and the water is less than approximately 10 dynes/cm. and is continued until a stable emulsion of droplets less than 2 microns average diameter results; and
   C. Removing substantially all of said solvent to define encapsulated colorant particles that are adapted to be formed as a film upon a textile surface and then set by application of heat sufficient to raise the polymer encapsulation above its glass transition temperature.

20. The process according to claim 19, wherein, in said mixing step, the polymer is soluble to less than 5 percent, in water, the solvent is soluble to less than 20% in water, and the amounts of polymer/colorant in said mixing step having a combined average density of approximately 1.0 gram/c.c., and said carrier fluid comprises water remaining after said solvent removal step.

21. The process according to claim 19, wherein, in said mixing step, the colorant comprises solid primary elements having an element average diameter range of between 0.01 and 1.0 microns and said dispersing is done with sufficient energy to disperse substantially one primary element as a core within a submicron sized polymer/solvent matrix wherein, further, the concentration ratio, by weight, of polymer to colorant for each resulting submicron sized encapsulated particle is between 0.1 and 10.0, and each particle density is controlled by the pigment to polymer ratio employed.

22. The process according to claim 19, wherein said polymer is thermoplastic and less than 5 percent soluble in water, and said dispersing step further comprises the addition of a surfactant, in the range between 0.1 percent and 20 percent, by weight, of colorant, and the concentration ratio, by weight, of polymer to encapsulated colorant for each submicron sized particle is between 0.1 and 10.0.

23. The process according to claim 19, wherein, in said mixing step, the concentration, by weight, of colorant to solvent is between 1.0 percent and 20 percent, said polymer has a viscosity of less than 200 centipoise when dissolved in said solvent and said dispersing step is done ultrasonically, until substantially each discontinuous phase droplet is less than 2 microns in average diameter and comprises a solvent/polymer matrix encapsulating colorant as a solid core.

24. The process according to claim 19 wherein said polymer is a thermosetting system of epoxy resin which requires a curing agent, said dispersing step comprises adding a cationic surfactant, and said curing agent is added in a continuous aqueous phase, in order to contact the dispersed polymer particle surfaces, whereby upon applying heat to particles that have been applied to a textile surface, the particles will thermoset upon said textile surface.

25. The process according to claim 24 wherein a cationic surfactant is used in said dispersing step and a water soluble curing agent is applied to said particles from a separate bath, after said particles have been applied to a substrate.

26. A textile colorant made by the process of claim 23.

27. A textile colorant made by the process of claim 24.

28. A process for encapsulating submicron sized pigment particles for use in cosmetics, wherein a polymer matrix surrounds a solid pigment particle and the resulting particles are in an aqueous suspension, said process comprising the steps of:
   A. Mixing together an organic solvent, a polymer soluble in said solvent but substantially insoluble in water and a pigment which substantially is insoluble in water to form a homogeneous mixture, wherein said solvent is characterized by a vapor pressure higher than water and said mixing is continued until said active ingredient has dispersed homogeneously in said solvent, without appreciable agglomeration; and
   B. Adding said solvent/polymer/pigment mixture, in a concentration range of 1.0% to 50.0%, by weight, to water which contains a nonionic surfactant and dispersing until an emulsion results wherein solvent/polymer/pigment droplets with an average diameter less than 5 microns comprise a discontinuous phase in water as the continuous phase, wherein said dispersing step is done under conditions where interfacial tension between the organic solvent and the water is less than approximately 10 dynes/cm.; and
   C. Removing substantially all of said solvents to define an aqueous mixture comprising encapsulated pigment in suspension; and
   D. Concentrating the encapsulated colorant to a desired concentration for admixture with a cosmetic carrier fluid.

29. The process according to claim 28 wherein said pigment comprises a metal oxide with an average primary particle size that is submicron, said polymer is soluble to less than 5 percent, in water, and said solvent is soluble to less than 20 percent in water.

30. The process according to claim 29 wherein said solvent is selected from the group consisting of methylene chloride and ethyl acetate, and said pigment is selected from the group consisting of oxides of iron, and pigments approved for cosmetic use.

31. The process according to claim 30 wherein said cosmetic carrier comprises the aqueous phase resulting from said solvent removal step, said polymer is non-film forming, said solvent is selected from the group consisting of methylene chloride and ethyl acetate, and said aqueous mixture comprises a dispersion of submicron polymer particles containing one or more primary pigment particles and non-pigmented polymer particles.

32. The process according to claim 29 wherein said polymer is film-forming, said solvent is selected from the group consisting of ethyl acetate and methylene chloride, and said aqueous mixture comprises a dispersion of submicron polymer particles containing one or more primary pigment particles, unencapsulated pigment and non-pigmented polymer particles.

33. A cosmetic made according to the process of claim 31.

34. A cosmetic made according to the process of claim 32.

* * * * *